(12) United States Patent
Regev et al.

(10) Patent No.: US 11,674,939 B2
(45) Date of Patent: Jun. 13, 2023

(54) DEVICES AND METHODS FOR QUANTIFYING NITRIC OXIDE

(71) Applicants: Gilly Regev, Vancouver (CA); Christopher C. Miller, North Vancouver (CA)

(72) Inventors: Gilly Regev, Vancouver (CA); Christopher C. Miller, North Vancouver (CA)

(73) Assignee: SaNOtize Research and Development Corp., Vancouver (CA)

( * ) Notice: Subject to any disclaimer, the term of this patent is extended or adjusted under 35 U.S.C. 154(b) by 542 days.

(21) Appl. No.: 16/541,084

(22) Filed: Aug. 14, 2019

(65) Prior Publication Data
US 2020/0110067 A1    Apr. 9, 2020

Related U.S. Application Data

(60) Provisional application No. 62/718,946, filed on Aug. 14, 2018.

(51) Int. Cl.
*G01N 33/00* (2006.01)
*G01N 1/22* (2006.01)
*G01N 21/76* (2006.01)

(52) U.S. Cl.
CPC .......... *G01N 33/0037* (2013.01); *G01N 1/22* (2013.01); *G01N 21/766* (2013.01); *G01N 33/0021* (2013.01)

(58) Field of Classification Search
CPC ... G01N 33/0037; G01N 33/0021; G01N 1/22
See application file for complete search history.

(56) References Cited

U.S. PATENT DOCUMENTS

| | | |
|---|---|---|
| 5,092,220 A | 3/1992 | Rounbehler |
| 5,248,616 A | 9/1993 | Beckman et al. |

(Continued)

FOREIGN PATENT DOCUMENTS

| | | |
|---|---|---|
| EP | 1798554 A | 6/2007 |
| WO | WO 2004/113892 | 12/2004 |

(Continued)

OTHER PUBLICATIONS

Coneski et al.; "Nitric oxide release part III. Measurement and reporting." Chem Soc Rev; May 21, 2012; vol. 41, Issue 10.

(Continued)

*Primary Examiner* — Christopher Adam Hixson
(74) *Attorney, Agent, or Firm* — Thorpe, North & Western, LLP; David W. Osborne

(57) ABSTRACT

The present disclosure relates to methods, devices, and systems for measuring nitric oxide released from a material. For example, a method of measuring nitric oxide release from a material can include introducing a continuous flow of a carrier gas into a sample holding chamber via a carrier gas inlet at an effective flow rate, introducing an amount of the nitric oxide releasing material into the sample holding chamber via a separate sample inlet to contact the continuous flow of the carrier gas, directing the carrier gas and released nitric oxide out of the sample holding chamber via a nitric oxide outlet toward a nitric oxide detector, and quantifying an amount of released nitric oxide using the nitric oxide detector.

10 Claims, 10 Drawing Sheets

(56) References Cited

U.S. PATENT DOCUMENTS

| | | | |
|---|---|---|---|
| 5,374,397 | A | 12/1994 | Termin |
| 9,753,019 | B2 | 9/2017 | Blomberg et al. |
| 10,537,697 | B2 | 1/2020 | Montgomery |
| 10,543,336 | B2 | 1/2020 | Miller |
| 10,661,045 | B2 | 5/2020 | Bathe |
| 10,751,364 | B2 | 8/2020 | Miller |
| 10,758,703 | B2 | 9/2020 | Kohlmarm |
| 11,304,972 | B2 | 4/2022 | Miller |
| 2011/0182970 | A1 | 7/2011 | Hyde et al. |
| 2014/0197043 | A1* | 7/2014 | Blomberg .......... G01N 33/0011 205/781 |
| 2014/0197044 | A1 | 7/2014 | Blomberg et al. |
| 2020/0282375 | A1 | 9/2020 | Fine |
| 2021/0038838 | A1 | 2/2021 | Acker |
| 2021/0145732 | A1 | 5/2021 | Minton |
| 2022/0040224 | A1 | 2/2022 | Miller |
| 2022/0054536 | A1 | 2/2022 | Miller |
| 2022/0088342 | A1 | 3/2022 | Fine |
| 2022/0160792 | A1 | 5/2022 | Bryan |

FOREIGN PATENT DOCUMENTS

| | | |
|---|---|---|
| WO | WO 2014/110605 A1 | 7/2014 |
| WO | WO 2018/049291 | 3/2018 |

OTHER PUBLICATIONS

Ghaffari et al.; "Potential application of gaseous nitric oxide as a topical antimicrobial agent." Nitric Oxide; Elsevier; Feb. 2006; vol. 14, Issue 1; pp. 21-29.

Ghaffari et al.; "Efficacy of gaseous nitric oxide in the treatment of skin and soft tissues infections." Wound Repair Regeneration; The International Journal of Tissue Repair and Regeneration; May 25, 2007; vol. 15, Issue 3; pp. 368-377.

Ghaffari et al.; "A direct nitric oxide gas delivery system for bacterial and mammalian cell cultures." Nitric Oxide; Elsevier; May 2005; vol. 12, Issue 3; pp. 129-140.

Miller.; "The antibacterial role of exogenous nitric oxide gas." University of British Columbia, (2004). (Abstract Only).

Miller et al.; "Gaseous nitric oxide bactericidal activity retained during intermittent high-dose short duration exposure." Nitric Oxide; Elsevier; Feb. 2009; vol. 20, Issue 1; pp. 16-23.

Miller et al.; "Inhaled nitric oxide decreases the bacterial load in a rat model of Pseudomonas aemginosa pneumonia." Journal of Cystic Fibrosis; Elsevier; Dec. 2013; vol. 12, Issue 6; pp. 817-820.

Miller et al.; "A phase I clinical study of inhaled nitric oxide in healthy adults." J Cyst Fibros; Elsevier; Jul. 2012; vol. 11, Issue 4; pp. 324-331.

Miller et al.; "Innate protection of *Mycobacterium smegmatis* against the antimicrobial activity of nitric oxide is provided by mycothiol." Antimicrob Agents and Chemotherapy; American Society for Microbiology; Sep. 2007; vol. 51, No. 9; pp. 3364-3366.

O'Donovan et al.; "Mitochondrial glutathione and oxidative stress: implications for pulmonary oxygen toxicity in premature infants." Mol Genet Metab; Elsevier; Sep. 2000; vol. 71, Issue 1-2; pp. 352-358.

Pacelli et al.; "Nitric oxide potentiates hydrogen peroxide-induced killing of *Escherichia coli*." J Exp Med; Nov. 1, 1995; vol. 182, Issue 5; pp. 1469-1479.

PCT Application No. PCT/IB2019/000939 Filing date Aug. 14, 2019; Gilly Regev, International Search Report; dated Jan. 16, 2020; 9 Pages.

Regev-Shoshani et al.; "A nitric oxide-releasing solution as a potential treatment for fungi associated with tinea pedis." J Appl Microbiol; Oct. 22, 2012; vol. 114, Issue 2; pp. 536-544.

Regev-Shoshani et al.; "Gaseous nitric oxide reduces influenza infectivity in vitro." Nitric Oxide; Elsevier; May 31, 2013; vol. 31; pp. 48-53.

Schairer et al.; "The potential of nitric oxide releasing therapies as antimicrobial agents." Virulence 2012; vol. 3, Issue 3; pp. 271-279.

Wink et al.; "Chemical biology of nitric oxide: Insights into regulatory, cytotoxic, and cytoprotective mechanisms of nitric oxide." Free Radical Biology and Medicine; Elsevier; Sep. 1998; vol. 25, Issues 4-5; pp. 434-456.

European Search Report; European Patent Application No. 19849447.8; dated Apr. 13, 2022; 9 pages.

\* cited by examiner

DEVICES AND METHODS FOR QUANTIFYING NITRIC OXIDE

BACKGROUND

Nitric Oxide (NO) is a small, unstable diatomic molecule. It measures about 115 picometers in its bond length, and is soluble in hydrophilic and hydrophobic environments. It has a free radical-like nature, a short half-life, and it is easily oxidized into nitrogen dioxide ($NO_2$). Within the body, nitric oxide can be endogenously produced by nitric oxide synthase enzymes (NOS), and is known to be involved in many physiological and pathological processes. For example, a low level of NO in the blood encourages vasodilation to prevent ischemic tissue damage, helps wound healing, and is an effective antimicrobial agent. Conversely, a high level of NO in the blood leads to tissue toxicity and contributes to inflammatory conditions like septic shock, diabetes, and arthritis.

DESCRIPTION OF EMBODIMENTS

Figure 1:
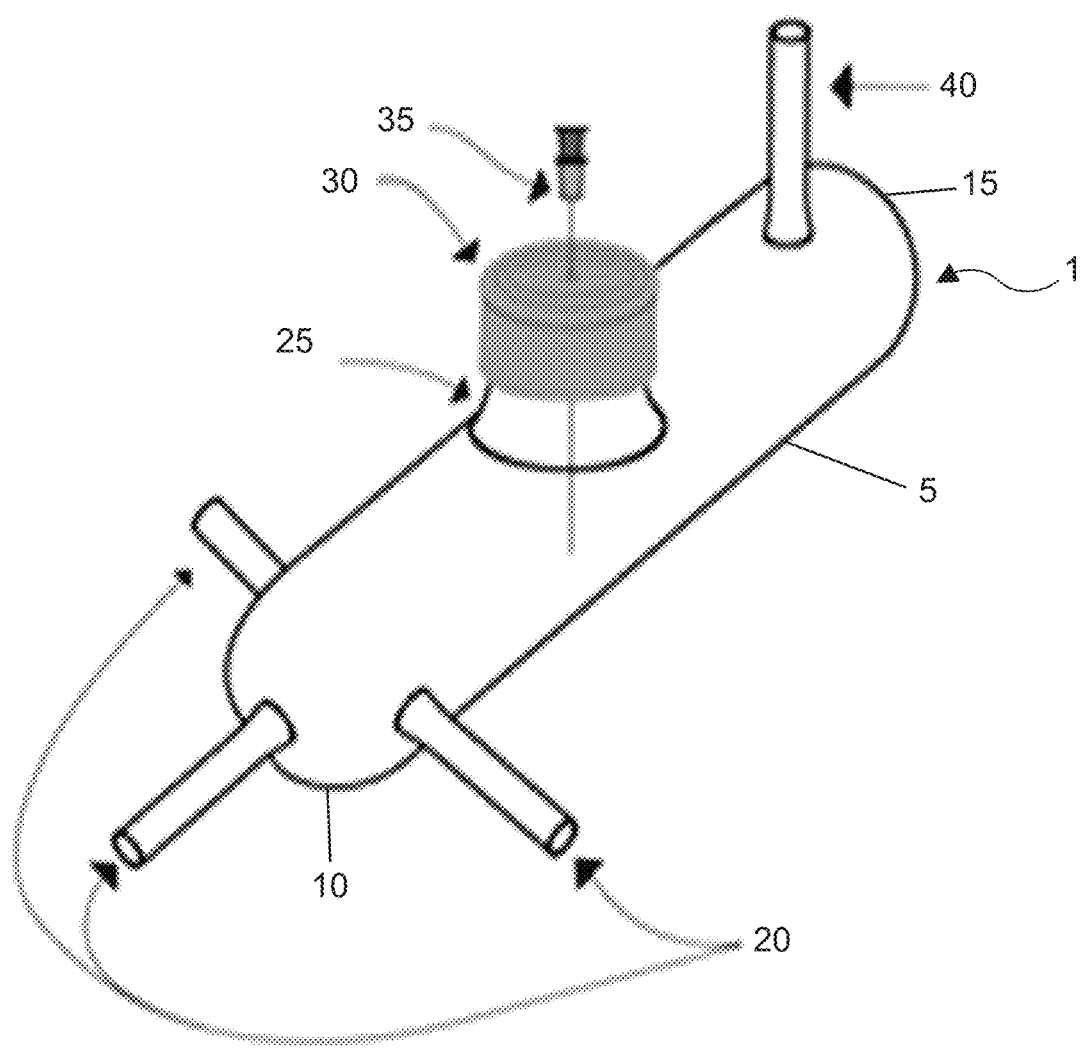
FIG. 1 depicts a nitric oxide collection device, in accordance with an example embodiment.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a sensor" includes a plurality of such sensors.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

The term "coupled," as used herein, is defined as directly or indirectly connected in an electrical or nonelectrical manner. "Directly coupled" structures or elements are in contact with one another and are attached. Objects described herein as being "adjacent to" each other may be in physical contact with each other, in close proximity to each other, or in the same general region or area as each other, as appropriate for the context in which the phrase is used.

As used herein, comparative terms such as "increased," "decreased," "better," "worse," "higher," "lower," "enhanced," "maximized," "minimized," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a stimulation process that has an "increased" therapeutic effect or result can refer to improved results or efficacy attained by the process as compared to a similar or different process intended for treatment of the same condition or experience.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "effective" refers to an amount, degree, action, or other parameter that is adequate to accomplish a stated or intended purpose. For example, an "effective amount" of nitric oxide refers to at least the minimum amount of nitric oxide that is sufficient or required to provide an intended effect, such as a therapeutic effect (e.g. treat a condition in a subject, eradicate or reduce the presence of microorganisms, etc.). Furthermore, an "effective flow rate" refers to at least the minimum rate at which a carrier gas or other fluid stream is applied in a given context, such as to and/or through analytical equipment in order to successfully analyze a sample for a given analyte using the equipment.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

The present disclosure is directed to a number of methods, devices, and systems for measuring nitric oxide release from a material. Nitric oxide gas has been shown to have a number of positive benefits. For example, nitric oxide (NO) is produced in the endothelium tissue of the human body as part of normal physiological processes. For instance, NO is an endogenous vasodilator i.e., an agent that widens the internal diameter of blood vessels. NO may also be used as a sterilizing agent. It has also been discovered that NO will interfere with or kill the growth of bacteria grown in vitro. NO can, however, be toxic to humans if it becomes present at excessive levels. Thus, administration of NO gas is carefully controlled and monitored to ensure that non-toxic, but therapeutically effective levels are appropriately delivered in a clinical setting.

It can be cumbersome to directly administer nitric oxide gas to a subject due to equipment set-up, constant connection of the subject to NO delivery equipment, potential for leaks, awkwardness of handling gas tanks, etc. Thus, it can be desirable and considerably more flexible to administer a nitric oxide releasing material to a subject that can produce non-toxic, but therapeutically effective levels of NO (e.g. in vivo) without having to be attached to a gas administration system during the treatment period, etc. Yet, while methods of directly monitoring non-toxic, but therapeutically effective levels of NO gas have been well defined, methods of characterizing nitric oxide release from NO releasing materials are still needed. Such characterization is particularly important for commercialization of products in order to establish and meet regulatory standards for specific therapies, safety data, quality control, etc. Accordingly, the present disclosure describes a number of devices, systems, and methods for measuring or characterizing NO release from a material.

As a further note, in the present disclosure, when discussing the various devices, systems, and methods, each of these discussions can be considered applicable to each of these examples, whether or not they are explicitly discussed in the context of that example. Thus, for example, in discussing details about the devices per se, such discussion also refers to the systems and methods, and vice versa.

Methods of measuring NO release from a material can include a variety of steps. For example, the methods can include introducing a continuous flow of a carrier gas into a sample holding chamber via a carrier gas inlet at an effective flow rate. The methods can also include introducing an amount of NO releasing material into the sample holding chamber via a separate sample inlet to contact the continuous flow of the carrier gas. The carrier gas and any NO released from the NO releasing material can be directed out of the sample holding chamber via a NO outlet and/or a sample outlet. In some examples, the carrier gas and released NO can be directed toward a NO detector to quantify the amount of released NO.

In further detail, a variety of carrier gases can be employed in the present methods, depending on the type of characterization studies desired to be performed. For example, in some cases, it can be desirable to measure NO production in an inert environment. In such examples, the carrier gas can be an inert carrier gas. Non-limiting examples of suitable inert carrier gases can include a noble gas (e.g. helium gas, neon gas, argon gas, krypton gas, xenon gas, radon gas), nitrogen gas, or other suitable inert gas. In other examples, it can be desirable to introduce a carrier gas that is not inert. Such non-inert carrier gases can be valuable for toxicological, environmental, or other suitable characterization studies. In such examples, the carrier gas can include gaseous mixtures to simulate ambient air, particular environmental conditions (e.g. with or without pollutants, various humidity levels, various carbon dioxide levels, etc.), or the like. Thus, in some examples, the carrier gas can include nitrogen, argon, oxygen, carbon dioxide, water vapor, the like, or various combinations thereof.

Regardless of the particular carrier gas employed, it can be desirable to prepare the sample holding chamber prior to introducing the carrier gas and/or NO releasing material to provide a more controlled testing environment. Various measures can be taken to prepare the sample holding chamber (e.g. to reduce the oxygen content, $CO_2$ content, etc. inside the sample holding chamber prior to introducing the carrier gas and/or NO releasing material). For example, a vacuum can be applied to the sample holding chamber to evacuate the sample holding chamber prior to introducing the carrier gas and/or the NO releasing material. In additional examples, the sample holding chamber can be flushed with an inert gas to reduce oxygen content within the sample holding chamber to 5% or lower, 1% or lower, or 0.5% or lower prior to introducing the carrier gas and/or the NO releasing material. In some further examples, the sample holding chamber can be purged of oxygen to substantially eliminate oxygen from the sample holding chamber. Where the sample holding chamber is purged, oxygen can be present in the sample holding chamber in an amount of 0.01% or less, 0.001% or less, or 0.0001% or less.

The carrier gas can be introduced into the sample holding chamber at a variety of effective flow rates. For example, in some cases, the carrier gas can be introduced into the sample holding chamber at an effective flow rate of from about 0.25 liters per minute (L/min) to about 15 L/min or higher. In some examples, the effective flow rate can be from about 0.025 L/min to about 1 L/min, from about 1 L/min to about 5 L/min, or from about 5 L/min to about 10 L/min. However, it is noted that the effective flow rate can be adjusted to achieve a NO level within a suitable (e.g. detectable, quantifiable, etc.) range. Thus, where the amount of NO released from the NO releasing material is high, it may be desirable to employ a higher effective flow rate to dilute the NO to a more suitable level within the headspace of the sample holding chamber and/or an outlet gas. In other examples, where the amount of NO released from the NO releasing material is low, it may be desirable to employ a lower effective flow rate to achieve a higher concentration of NO in the headspace of the sample holding chamber and/or an outlet gas. It is further noted that the present methods can also include measuring a flow rate of a carrier gas into the sample holding chamber, measuring a flow rate of an outlet gas out of the sample holding chamber, or both.

In some examples, the carrier gas can be introduced into the sample holding chamber via a single carrier gas inlet. In other examples, the carrier gas can be introduced into the sample holding chamber via a plurality (e.g. 2, 3, 4, etc.) of carrier gas inlets simultaneously. Regardless of the number of carrier gas inlets, it can be desirable to minimize or eliminate laminar flow to promote homogeneous mixing of gases within the sample holding chamber. Thus, where the carrier gas is introduced into the sample holding chamber via a single carrier gas inlet, it can be desirable to employ a diffuser or other suitable mixing device to promote homogeneous mixing or to minimize or eliminate laminar flow. Where a plurality of inlets is employed, it can be possible to position the plurality of inlets relative to one another to promote homogeneous mixing without the need of a diffuser, although a diffuser may still be used as desired. For example, in some cases, the diffuser and/or positioning of the inlets can promote a homogeneous flow having a Reynolds number of greater than 2000, greater than 3000, greater than 3500, greater than 4000, or greater than 4500. In some examples, homogeneous mixing can be monitored or verified by positioning various NO sampling ports throughout the sample holding chamber to verify equivalent or approximately equivalent NO concentrations at each position within the sample holding chamber.

The carrier gas can be introduced into the sample holding chamber before, contemporaneously with, or after introducing the NO releasing material, depending on the type of testing desired to be performed. It is noted that the NO releasing material can include active and/or inactive materials. By "active," it is meant that the material is in a state and/or form that readily produces nitric oxide. By "inactive," it is meant that the material is in a state and/or form that does not produce nitric oxide, or that minimally produces nitric oxide. Thus, in some examples, an inactive NO releasing material or component can be introduced into the sample holding chamber that is subsequently activated by an activating component. As such, in some examples, the NO releasing material can be activated in situ within the sample holding chamber. For example, a first component of the NO releasing material can be introduced prior to introducing a second component of the NO releasing material such that the NO releasing material is activated upon combination of the first and second components. Thus, in some examples, the first component can be introduced into the sample holding chamber prior to or contemporaneous with introducing the carrier gas and the second component can be introduced into the sample holding chamber contemporaneous with or after introduction of the carrier gas. In other examples, the first and second components can be introduced separately into the sample holding chamber, but both prior to introducing the carrier gas. In yet other examples, the first and second components can be introduced separately into the sample holding chamber, but both contemporaneously with introducing the carrier gas (e.g. via separate sample inlets). In still other examples, the first and second components can be introduced separately into the sample holding chamber, but both after introducing the carrier gas. Where first and second components are introduced into the sample holding chamber separately, they can be introduced either sequentially or contemporaneously, as desired. As one specific and non-limiting example, a NO releasing solution can include a NO-releasing component (e.g. a nitrite) and an acidifying component. The NO-releasing component and the acidifying component can be combined to activate the NO releasing solution. With this in mind, the NO-releasing component and the acidifying component can be combined and activated either prior to, contemporaneously with, or after introduction into the sample holding chamber. Where they are combined and activated after introduction into the sample holding chamber, either the NO-releasing component or the acidifying component can be added prior to or contemporaneously with the other, as desired. In still further examples, the NO-releasing component, the acidifying component, or both can be added prior to, contemporaneously with, or after introduction of the carrier gas, as desired.

A variety of NO releasing materials can be introduced into the sample holding chamber. Non-limiting examples can include a liquid, a solid, a semi-solid, a gel, a cream, or the like. In some examples, the NO releasing materials can be held in a container or other support structure, such as a vial, a sponge, a fibrous material (e.g. cloth or paper towel), etc. In some examples, the NO releasing materials can be or include NO releasing polymers, a plastic, a gel, or the like. In some additional examples, the NO releasing materials can include a nitrite, such as sodium nitrite, potassium nitrite, barium nitrite, calcium nitrite, mixed salts of nitrite such as nitrite orotate, nitrite esters such as amyl nitrite, the like, or a combination thereof. In yet additional examples, the NO releasing material can include an acidifying agent, such as ascorbic acid, salicylic acid, malic acid, lactic acid, citric acid, formic acid, benzoic acid, tartaric acid, carbonic acid, hydrochloric acid, sulfuric acid, nitric acid, nitrous acid, phosphoric acid, the like, or a combination thereof. Generally, measurement or characterization of NO release from any suitable material can be performed using the methods described herein, and any suitable material is considered to be within the present scope.

The NO releasing material can be introduced in a number of ways. In some examples, the NO releasing material can be introduced into the sample holding chamber as a bolus (i.e. all at once). In other examples, the NO releasing material can be introduced into the sample holding chamber by metering the material into the sample holding chamber at a desired rate. In additional examples, the NO releasing material can be introduced into the sample holding chamber by injecting, flowing, pouring, dumping, depositing, placing, positioning, etc., the NO releasing material in the sample holding chamber.

The NO releasing material can be introduced into the sample holding chamber in a variety of amounts, depending on the size of the sample holding chamber, the particular testing desired to be performed, etc. In some examples, the NO releasing material can be introduced into the sample holding chamber in an amount of from about 1 microliter (µl) to about 1000 milliliters (ml). In some specific examples, the NO releasing material can be introduced into the sample holding chamber in an amount from about 10 µl to about 100 µl, from about 100 µl to about 500 µl, from about 500 µl to about 1 ml, from about 1 ml to about 10 ml, from about 10 ml to about 100 ml, from about 100 ml to about 500 ml, or from about 500 ml to about 1000 ml. In other examples, the NO releasing material can be introduced into the sample holding chamber in an amount from about 1 microgram (m) to about 1000 milligrams (mg). In some specific examples, the NO releasing material can be introduced into the sample holding chamber in an amount from about 10 µg to about 100 µs, from about 100 µg to about 500 µg, from about 500 µg to about 1 mg, from about 1 mg to about 10 mg, from about 10 mg to about 100 mg, from about 100 mg to about 500 mg, or from about 500 mg to about 1000 mg.

The carrier gas can be directed to contact the NO releasing material in a number of ways. For example, in some cases, the carrier gas can be directed to flow over and/or around the NO releasing material. In some examples, the carrier gas can be directed to flow/bubble into and/or through the NO releasing material. In some examples, a combination of these methods can be employed. As will be described in greater detail in the Examples section, different metrics can be measured with different interactions of the carrier gas with the NO releasing material. As non-limiting examples, the present methods can be used to measure the maximum peak level for the NO, the rate the NO release, duration of NO levels above/below a predetermined threshold value, total NO released during a predetermined time period, total NO released, etc.

NO can be directed toward a NO detector in a number of ways. For example, in some cases, the NO can be sampled from a headspace of the sample holding chamber (e.g. using a syringe or other gas transfer device) and transferred to a NO detector for sample analysis. In some examples, the NO detector can be fluidly connected to the sample holding chamber and the NO can be directed to the NO detector via a fluid channel. It is noted that the fluid channel is not generally configured as a separations channel (e.g. a chromatographic column), but a separations channel can be employed in some circumstances. In some specific examples, the mainstream outlet can be directly fluidically connected to a NO detector or other suitable detector. In some additional examples, a split or sidestream channel can be plumbed from the mainstream channel to the NO detector or other suitable detector. Thus, NO can be directed toward a NO detector via a mainstream channel, a sidestream channel, or both. Where a sidestream channel is employed, the mainstream channel and sidestream channel can typically have a volumetric split ratio of from about 99:1 to 50:50 for mainstream: sidestream flows. In some specific examples, the mainstream channel and sidestream channel can have a volumetric split ratio of from about 20:1 to about 10:1, from about 10:1 to about 5:1, from about 8:1 to about 3:1, from about 5:1 to about 1:1 or from about 3:1 to about 1:1. In some further examples, the specific split ratio can be determined by the maximum concentration detectable/measurable by the detector. For instance, an analyzer may have an upper detectability limit of 2000 ppm, but a reaction produces up to 10,000 ppm of analyte. In this particular example, a split ratio of 5:1 can be used for sidestream analysis to obtain a suitable level of analyte for detection. In some further examples, a sample can be withdrawn from the mainstream channel (e.g. via a syringe or other transfer device) and transferred to a NO detector. In some examples, the NO detection of the present methods can have a lower limit of quantitation (LLOQ) of 100 parts per billion (ppb) or less, 50 ppb or less, 10 ppb or less, or 1 ppb or less. Further, the NO detection can typically have an upper limit of quantification (ULOQ) of 1000 parts per million (ppm) or greater, 1500 ppm or greater, or 2000 ppm or greater.

The NO detector or another suitable detector can be used to measure other quantities as desired. For example, in some cases, the present methods can also be used to measure $O_2$ levels, $NO_2$ levels, etc. For example, $O_2$ levels can be measured to ensure that oxygen is not inadvertently being introduced into the sample holding chamber, as oxygen can affect NO production from the NO releasing material. In some additional examples, $NO_2$ levels can be measured to ensure that any $NO_2$ levels generated from the NO releasing material remain below 5 ppm, below 2.5 ppm, below 1 ppm, or lower (e.g. at a target level of NO production, at ambient conditions, etc.).

Various sample analysis times can be suitable. For example, a sample analysis time of from about 1 minute to about 24 hours can typically be suitable, though other sample analysis times can be used as desired. In some specific examples, the sample analysis time can be from about 5 minutes to about 30 minutes, from about 10 minutes to about 60 minutes, from about 60 minutes to about 6 hours, from about 6 hours to about 12 hours, or from about 12 hours to about 24 hours.

In some examples, the methods can also include controlling or regulating a temperature of the sample holding chamber and/or NO releasing material. In some specific examples, the temperature of the sample holding chamber and/or NO releasing material can be controlled or regulated to from about 5° C. to about 40° C. In some specific examples, the temperature of the sample holding chamber and/or NO releasing material can be controlled or regulated to from about 10° C. to about 20° C., from about 20° C. to about 30° C., or from about 30° C. to about 40° C. In some additional examples, the temperature of the sample holding chamber and/or NO releasing material can be controlled or regulated to from about 35° C. to about 40° C.

In some additional examples, the temperature within the sample holding chamber and/or the temperature of the NO releasing material can be monitored. In still additional examples, the sample holding chamber and/or the NO releasing material can be agitated or otherwise manipulated to promote mixing of the NO releasing material, reduce anomalous NO production spikes due to external vibrations or perturbances, or the like. Various other measurements and/or manipulations of or within the sample holding chamber and/or NO releasing material can also be performed, as desired.

The methods disclosed herein can be performed using a number of devices and systems. For example, NO collection devices are described that can be useful in the methods disclosed herein. The NO collection devices can include a sample holding chamber having an interior surface that is inert to NO. The sample holding chamber can also be configured to receive a NO releasing material therein. A sample inlet can be configured to allow passage of a NO releasing material into the sample holding chamber. A carrier gas inlet can be in fluid communication with the sample holding chamber. A NO outlet can also be in fluid communication with the sample holding chamber.

One non-limiting example of a NO collection device is illustrated in FIG. 1. The collection device 1 can include a sample holding chamber 5, which in some embodiments, can be formed as a unitary (e.g. single piece) structure, and in other examples, the structure can be modular (e.g. multiple joined pieces). Moreover, it should be noted that the collection device 1 can either be made as a unitary (e.g. single piece) structure, or as a modular (e.g. multiple joined pieces) structure. In this example, the sample holding chamber has an elongated shape with rounded opposing ends, such as inlet end 10 and outlet end 15. It is to be understood however, that the sample chamber can take any shape and/or size required to successfully achieve a specifically desired analysis or process. For example, the chamber can be rectangular, circular, square, pointed, etc. Furthermore, the interior volume of the sample chamber can be any desired volume to accommodate an analysis that requires a particular scale, flow rate, etc. to successfully detect a given analyte in a sample.

A plurality of carrier gas inlets (flow inlets) 20 are coupled to, or otherwise contiguously formed with, the sample holding chamber 5 at the flow inlet end 10. While three inlets are shown, it should be noted that any number of inlets required to provide a desired fluid flow or internal flow parameter (e.g. turbulence pattern, flow path, etc.) within the sample holding chamber 5 can be used. For example, 1, 2, 3, 4, 5, 6, or more flow inlets can be used. Moreover, the flow inlets 20 can be positioned at any desirable position at or around the flow inlet end 10 of the sample holding chamber 5. As depicted, one flow inlet is positioned with a flow axis substantially parallel to a central longitudinal axis of the sample chamber 5 and two other flow inlets positioned substantially opposite one another on opposing sides of sample chamber 5 and having a flow axis substantially perpendicular to a central longitudinal axis of the sample chamber 5. However, it is to be understood that the flow inlets can positioned at any location and with any flow axis (i.e. axis of direction along with a carrier gas will flow and enter the sample chamber) desired or required in order to accomplish or provide a specific effect, such as a flow parameter (e.g. turbulence pattern, flow path or direction, etc. In some embodiments, the flow inlets 20 can simply be apertures in the sample chamber 5, and in other embodiments, the flow inlets can include elongated tubular structures as depicted in FIG. 1.

At least one sample inlet/outlet 25 is provided in fluid communication with the sample chamber 5. As shown in FIG. 1, a single sample inlet/outlet 25 is positioned at an approximate midway point between the inlet end 10 and the outlet end 15 of the sample chamber 5. However, it should be noted that the sample inlet/outlet 25 can be positioned at any specific location between the flow inlet and outlet ends 10, 15. As shown, the sample inlet/outlet 25 is also contiguously formed with the sample holding chamber. While the sample inlet/outlet is shown as a tubular protrusion, it should be noted that like with the other inlets/outlets associated with the sample chamber 5, the sample inlet/outlet 25 can take any shape or configuration desired or needed to achieve a specific result or performance and may simply be an aperture. In the present embodiment, a rubber septum 30 is used to fluidly seal the sample inlet/outlet and a syringe/needle 35 is employed to introduce/withdrawn samples. Again, various specific structures can be used in connection with the sample inlet/outlet 25 to effect closure or regulation of entrance/exit of a specific sample. For example, instead of a stopper, a valve, port, cap, cork, film, barrier, hatch, or door, etc. can be used to control ingress and egress of a sample and any suitable support apparatus can be used in place of the needle/syringe, such as a spoon, tube, beaker, test tube, petri dish, or other device that is capable of effectively presenting a sample to the sample inlet/outlet 25.

As depicted in FIG. 1, the outlet end 15 of the sample chamber 5 includes a single NO outlet (flow outlet) 40 is contiguously formed with the sample holding chamber 5. As with the flow inlets 20, the flow outlet can take any needed shape or have any needed location at or near the outlet end 15 including all the configurations previously described for the flow inlets 20. For example, as shown, the flow outlet 40 is positioned on the same side of the sample chamber 5 as the sample inlet/outlet 25 and has a flow axis parallel thereto (e.g. perpendicular to a flow axis of the sample chamber 5). However, any position or flow axis that is desirable can be used, including flow axes that are parallel with or perpendicular to the flow axis of the sample chamber 5, and/or the flow inlet ports. Furthermore, a plurality of flow outlets can be used, for example, 1, 2, 3, 4, 5, 6, or more flow outlets can be used, and in some embodiment, the flow outlet can merely be an opening in the sample chamber 5.

In some specific examples, this particular configuration of a NO collection device can be used to flow a carrier gas over and/or around a NO releasing material disposed within the sample holding chamber. This particular configuration may also be used in other ways as well.

Figure 2:
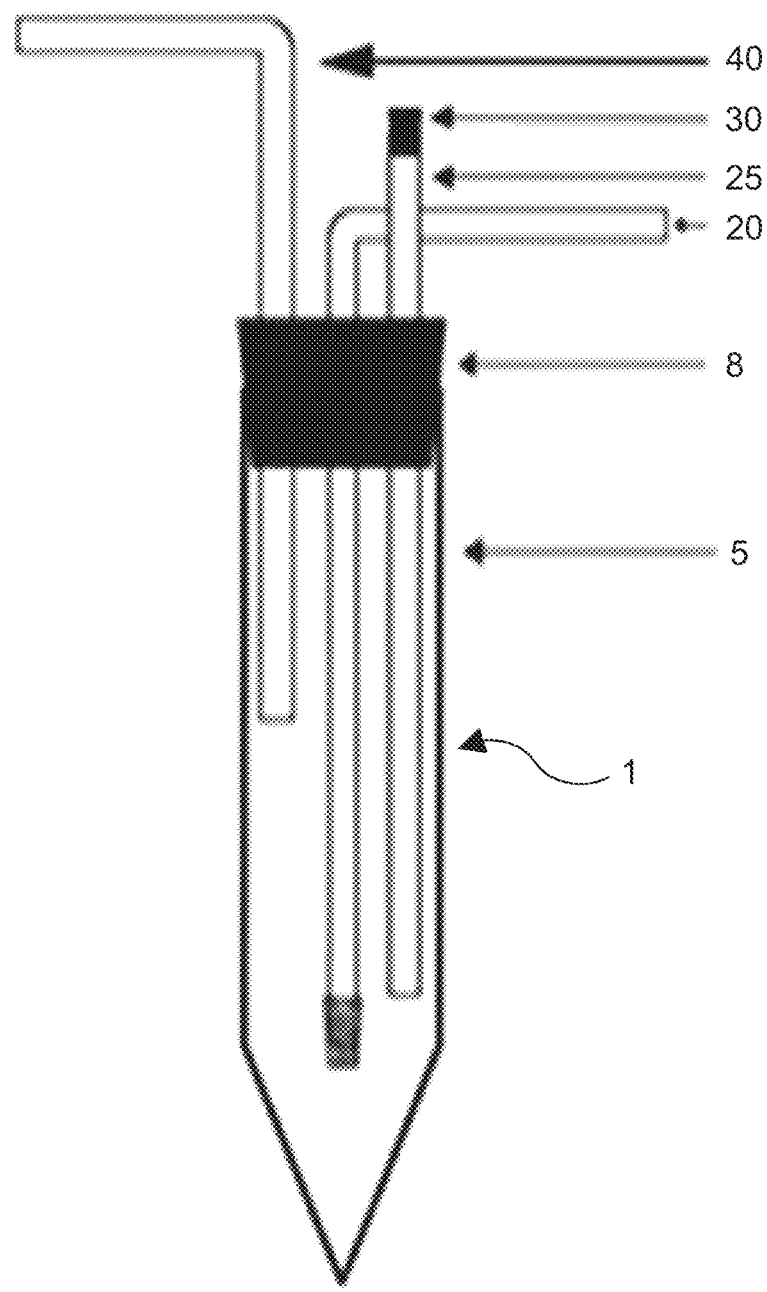
FIG. 2 depicts a nitric oxide collection device, in accordance with an example embodiment.

Another non-limiting example of an embodiment of a NO collection and/or analysis/detection or sample/collection device is illustrated in FIG. 2. In this particular example, the collection device 1 can include a sample holding chamber 5 that is defined by the sample or NO receptacle (e.g. a bubbler vial) and a lid (e.g. a rubber stopper). A single, separately formed carrier gas inlet (flow inlet) 20 can extend into the sample holding chamber 5 via the lid 8. In this particular example, the carrier gas inlet 20 can include a porous terminus positioned within the sample holding chamber. A single, separately formed NO outlet (flow outlet) 40 can extend from the sample holding chamber 5 to an exterior location via the lid 8. A single, separately formed sample inlet/outlet 25 can also extend into the sample holding chamber via the lid 8. In some specific examples, the particular device illustrated in FIG. 2 can be used to bubble/flow a carrier gas into and/or through a NO releasing material. This particular configuration may also be used in other ways as well. It is to be understood that each of the components/elements of the collection device as shown in FIG. 2 can have the same alterations or adjustments to the various elements or components as mentioned regarding the elements of FIG. 1, for example with respect to number, direction, positioning, and relationship of the elements shown. For example, a plurality of flow inlets 20 can be used, a plurality of flow outlets 40 can be used, and the material of the lid can be a rubber stopper or can be a door, port, fitting, etc.

Thus, the NO collection device can have a number of shapes, sizes, and configurations, depending on the desired testing to be performed with the device. For example, in some cases, the sample holding chamber can be defined by a single unitary structure, as illustrated in FIG. 1. In other examples, the sample holding chamber can be defined by a plurality of structures coupled together, such as a NO receptacle and a lid, as illustrated in FIG. 2, for example.

Whatever the shape or size, the interior surface of the sample holding chamber can be inert to NO. In some examples, this can be accomplished by fabricating the NO collection device out of materials that are inert to NO (e.g. glass, etc.). In other examples, the sample holding chamber can include an inert liner positioned to line the interior surface of the sample holding chamber. In some examples, the inert liner can include or be made of an epoxy polymer, phenol epoxy, a vinyl polymer, a rubber, a polyamide-imide (PAM), an acrylic polymer, polytetrafluoroethylene, the like, or a combination thereof. It is further noted that one or more gas inlets/outlets and/or sample inlets/outlets can be fabricated out of materials that are inert to NO and/or lined interiorly and/or exteriorly with a liner that is inert to NO. In some specific examples, all surfaces of the carrier gas inlet, the sample inlet, an optional sample outlet, the nitric oxide outlet, or a combination thereof that contact or are intended to contact the NO releasing material and/or released NO gas can be fabricated of or lined with a material that is inert to NO.

The NO collection device can include one or more sample inlets, which in some examples can double as sample outlets. In other examples, the NO collection device can include one or more designated sample inlets and one or more designated sample outlets. In some examples, one or more sample inlets and/or sample outlets can be contiguously formed with the sample holding chamber. In some examples, one or more sample inlets and/or one or more sample outlets can be separately formed, but can be fluidly connected to the sample holding chamber. In some specific examples, one or more sample inlets and/or sample outlets can extend into the sample holding chamber. In some further examples, one or more sample inlets and/or one or more sample outlets can include a stopper, a septum, a filter, a syringe, a needle, the like, or a combination thereof.

In some examples, the NO collection device can include a single carrier gas inlet (e.g. in FIG. 2). In other examples, the NO collection device can include a plurality (e.g. 2, 3, 4, etc.) of carrier gas inlets (e.g. in FIG. 1). In some examples, where the NO collection device includes a plurality of carrier gas inlets, the carrier gas inlets can be positioned at angles relative to one another to promote homogenous mixing of the carrier gas within the sample holding chamber. As described above, it can be desirable to minimize laminar flow within the sample holding chamber. As such, a diffuser, a plurality of carrier gas inlets, or a combination thereof can be employed to help promote homogeneous mixing and minimize laminar flow. In some specific examples, where a plurality of carrier gas inlets is employed, individual carrier gas inlets can be positioned at an angle of from about 30° to about 180°, from about 50° to about 150°, or from about 60° to about 120° relative to adjacent carrier gas inlets. In some examples, one or more carrier gas inlets can be formed separately from the sample holding chamber, but can be fluidly connected to the sample holding chamber. In some specific examples, one or more carrier gas inlets extend into the sample holding chamber. In other examples, one or more carrier gas inlets can be contiguously formed with the sample holding chamber.

The NO collection device can also include one or more NO outlets. In some examples, one or more NO outlets can be formed separately from the sample holding chamber, but can be fluidly connected to the sample holding chamber. In some specific examples, one or more NO outlets extend into the sample holding chamber. In other examples, one or more NO outlets can be contiguously formed with the sample holding chamber. In some further examples, the NO collection device can include an over-pressure exhaust valve to vent the sample holding chamber prior to reaching a damaging internal pressure.

In some examples, the NO collection device can further include a mass flow meter positioned and configured to measure an inlet flow of a carrier gas flowing into the sample holding chamber. In some additional examples, the NO collection device can include a mass flow meter positioned and configured to measure an outlet flow exiting the sample holding chamber.

In still additional examples, the NO collection device can include a temperature sensor positioned and configured to measure a temperature of or within the sample holding chamber. Non-limiting examples of temperature sensors can include thermistors, resistive temperature detectors (RTDs), thermocouples, the like, or a combination thereof. In some further examples, the NO collection device can include a temperature regulator configured to control a temperature of or within the sample holding chamber. Non-limiting examples of temperature regulators can include resistive heaters, heat transfer fluids and associated jackets/networks, peltier coolers, the like, or a combination thereof.

In some examples, the NO collection device can further include a variety of additional sensors. In some specific examples, the NO collection device can include an oxygen sensor. In some additional specific examples, the NO collection device can further include a $NO_2$ sensor. In other examples, these sensors can be included in a NO measurement system.

NO measurement systems can include a NO collection device as described herein and a NO detector. In some examples, the NO detector can be fluidly coupled to the NO collection device. In other examples, the NO detector can be configured to analyze a sample that is withdrawn or sampled from the NO collection device and transferred directly to the NO detector. Where the NO detector is fluidly coupled to the NO collection device, the NO detector can be fluidly connected via a mainstream channel or a sidestream channel split off of the mainstream channel.

A variety of NO detectors can be employed in the NO measurement systems. Some non-limiting examples of NO detectors can include a chemiluminescence detector, an electrochemical detector, a fluorescence detector, a mass spectrometer, the like, or a combination thereof. As described above, in some examples, the NO systems can also include oxygen detectors, $NO_2$ detectors, the like, or a combination thereof. In some examples, a NO detector can double as an oxygen detector, a $NO_2$ detector, or the like.

In some examples, the NO measurement systems can be configured to have a lower limit of quantitation (LLOQ) for NO of 100 parts per billion (ppb) or less, 50 ppb or less, 10 ppb or less, or 1 ppb or less. Further, the NO measurement systems can be configured to have an upper limit of quantitation (ULOQ) for NO of 1000 parts per million (ppm) or greater, 1500 ppm or greater, or 2000 ppm or greater.

In some additional examples, the NO measurement systems can further include a carrier gas source fluidly coupled to the NO collection device at the carrier gas inlet(s). In some examples, the carrier gas source can be an inert carrier gas source. In other examples, the carrier gas source can include a plurality of carrier gas source that are premixed at ratios to provide a particular testing environment (e.g. to simulate ambient air, to simulate a particular environmental condition, etc.).

EXAMPLES

Example 1—Quantifying NO Using Two Different Nitric Oxide Sampling Chambers

NO production from a nitric oxide releasing solution (NORS) was characterized using two different NO sampling chambers connected to a chemiluminescence NO analyzer. One NO sampling chamber was designed as a flow-over device, such as the sampling chamber illustrated in FIG. 1. The second NO sampling chamber was designed as a bubbler-type device, such as the sampling chamber illustrated in FIG. 2.

The flow over device was used to measure the release of NO from a constant volume of NORS with a flow of nitrogen carrying the released NO to the chemiluminescence detector. With this device, the following metrics were quantified:

max peak (ppb),
the slope
the total of NO released during 30 min.

These metrics allow for the characterization of any NORS solution and allow quality control for the NORS. Further, this can establish manufacturing specification criteria and source ingredient controls to determine batch acceptability.

The bubbler-type device was designed and used to determine the amount of NO that a certain NORS can produce, within 1 hour (97% of total based on 3 hours experiments). This shows the max potential of a certain volume and strength of NORS to produce NO.

Measurements were performed injecting 5 mL of a nitric oxide releasing solution into the flow-over and bubbler-type device. Each vessel had three repetitions per day over six days for a total of 18 replicates. The max peak, NO production after 30 minutes, and slope after 1 minute was obtained from the flow-over device. The area under the curve was obtained from the bubbler-type device.

All data was analyzed using GraphPad Prism 6 and ranges of two (warning) and three (failed) standard deviations were calculated. In further detail, means and ranges were successfully calculated for max peak, NO production post-30 minute injection, slope and the area under the curve. A range of ±2 standard deviations suggest 95% of all tests should fall within the range. A range of ±3 standard deviations suggest 99.7% of all tests should fall within the range. It is suggested to retake a measurement falling between the two ranges to confirm the product is of passable quality. Any measurement falling outside ±3 standard deviations will require further investigation and perhaps voiding the entire lot.

Figure 3:
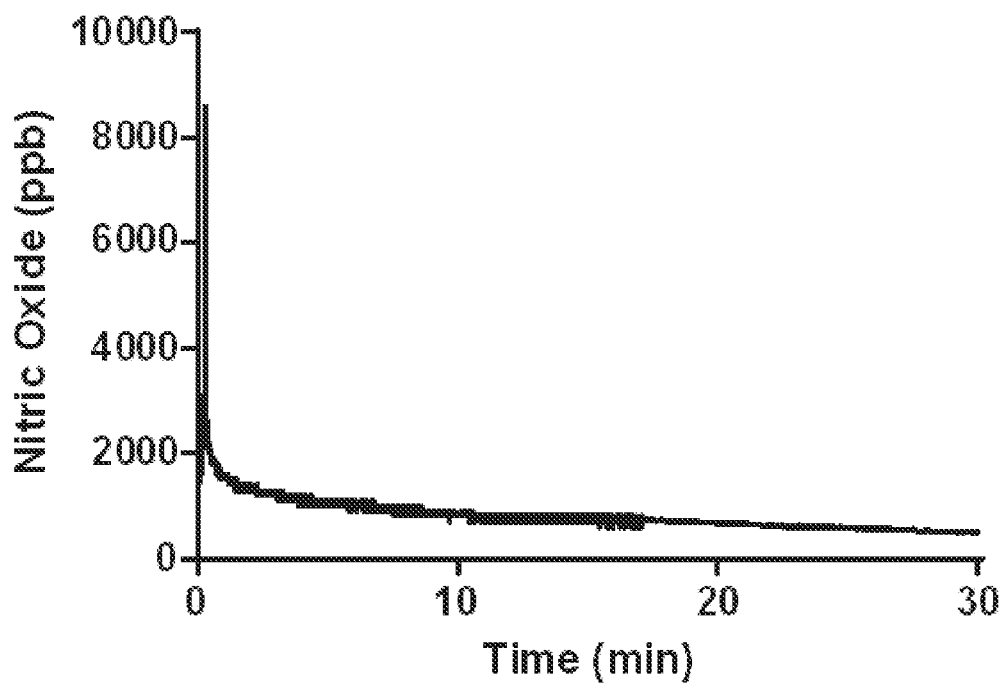
FIG. 3 is a graph of nitric oxide (ppb) measurement data obtained by introducing 5 mL of a nitric oxide releasing solution into the sampling chamber of a nitric oxide collection device as represented in FIG. 1.
Figure 4:
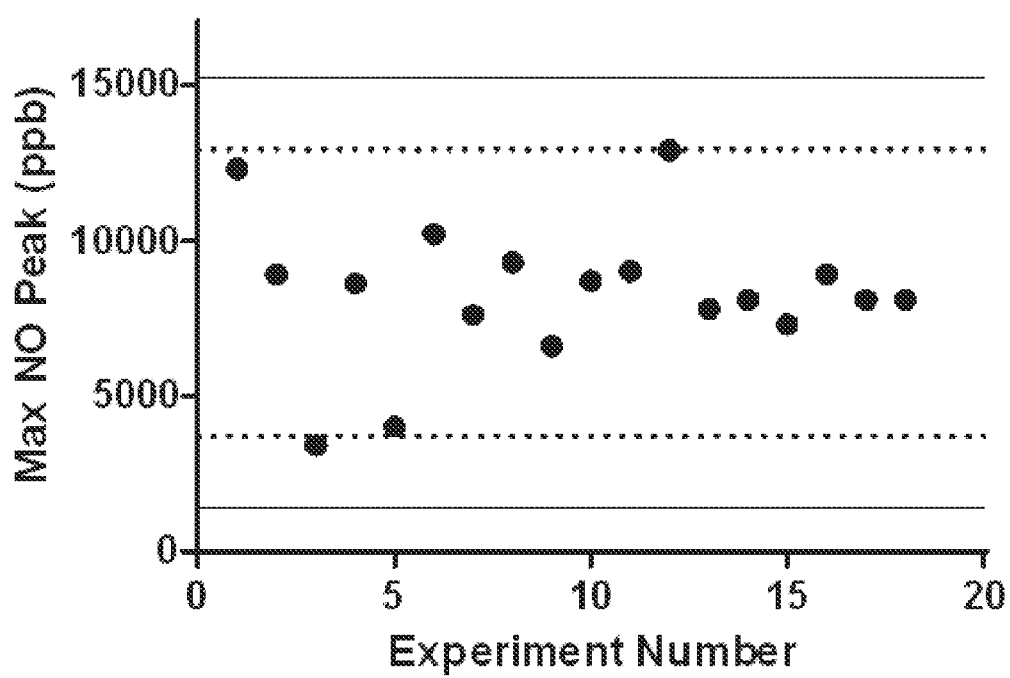
FIG. 4 represents the maximum nitric oxide (NO) peak (ppb) measurement data obtained from introducing 5 mL of a nitric oxide releasing solution into the sampling chamber of a nitric oxide collection device as represented in FIG. 1, with warning (dotted) and failure (solid) lines added signifying two and three standard deviations respectively.
Figure 5:
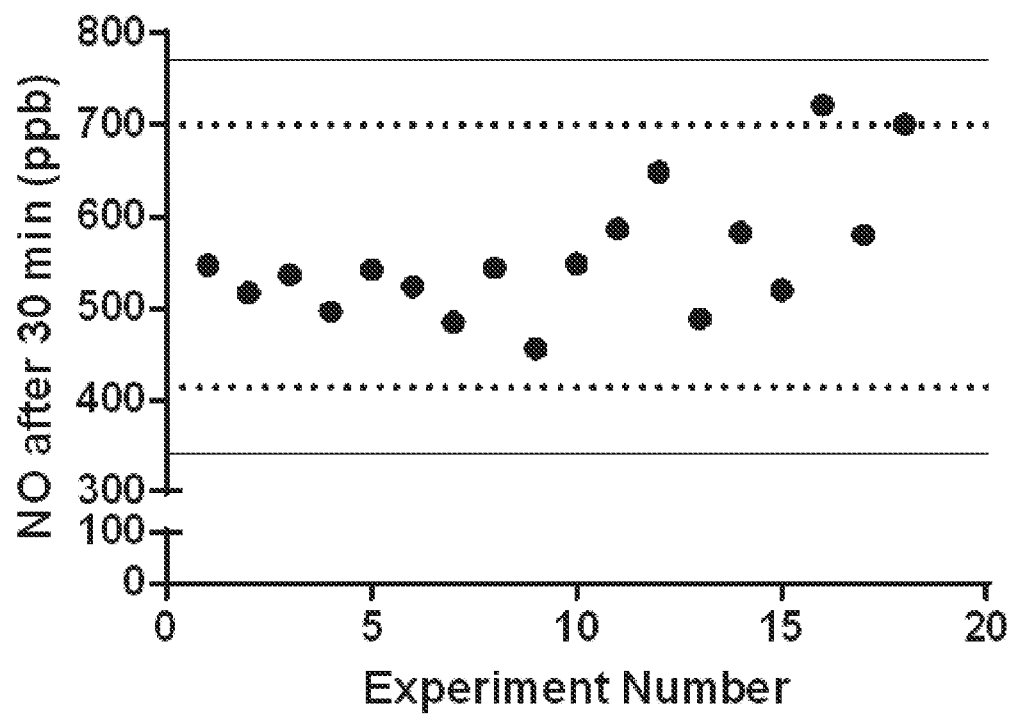
FIG. 5 represents NO production (ppb) after 30 minutes of measuring, obtained from introducing 5 mL of a nitric oxide releasing solution into a nitric oxide collection device as represented in FIG. 1, with warning (dotted) and failure (solid) lines added signifying two and three standard deviations respectively.
Figure 6:
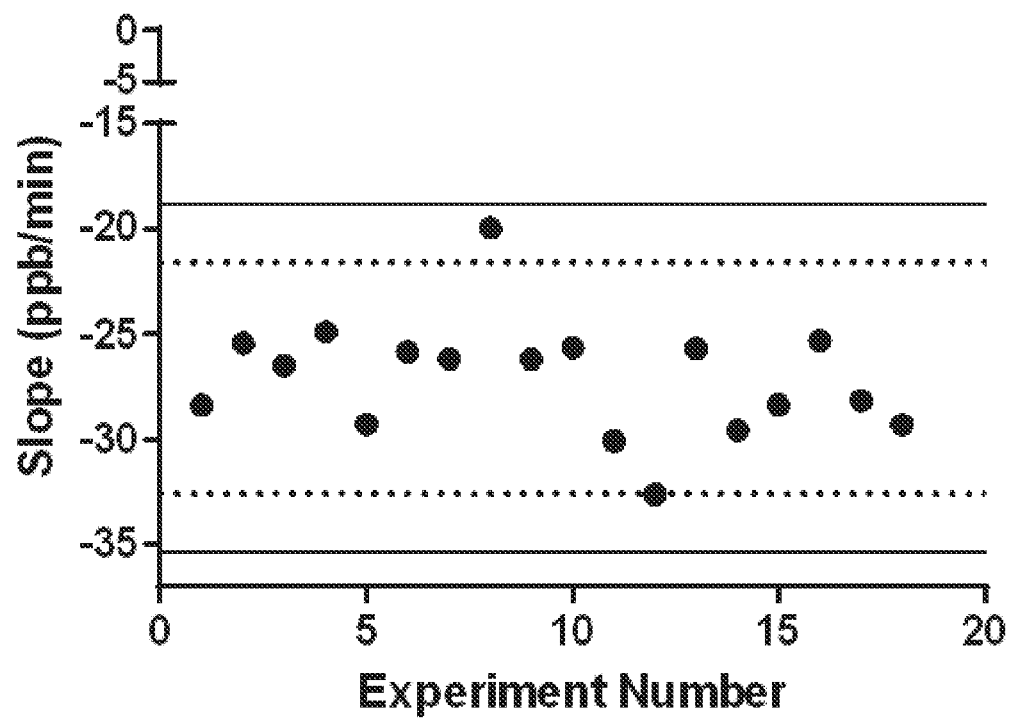
FIG. 6 represents the slope NO (ppb/min) calculated from 1-30 minutes post introduction, obtained from injecting 5 mL of a nitric oxide releasing solution into a nitric oxide collection device as represented in FIG. 1 with warning (dotted) and failure (solid) lines added signifying two and three standard deviations respectively.
Figure 7:
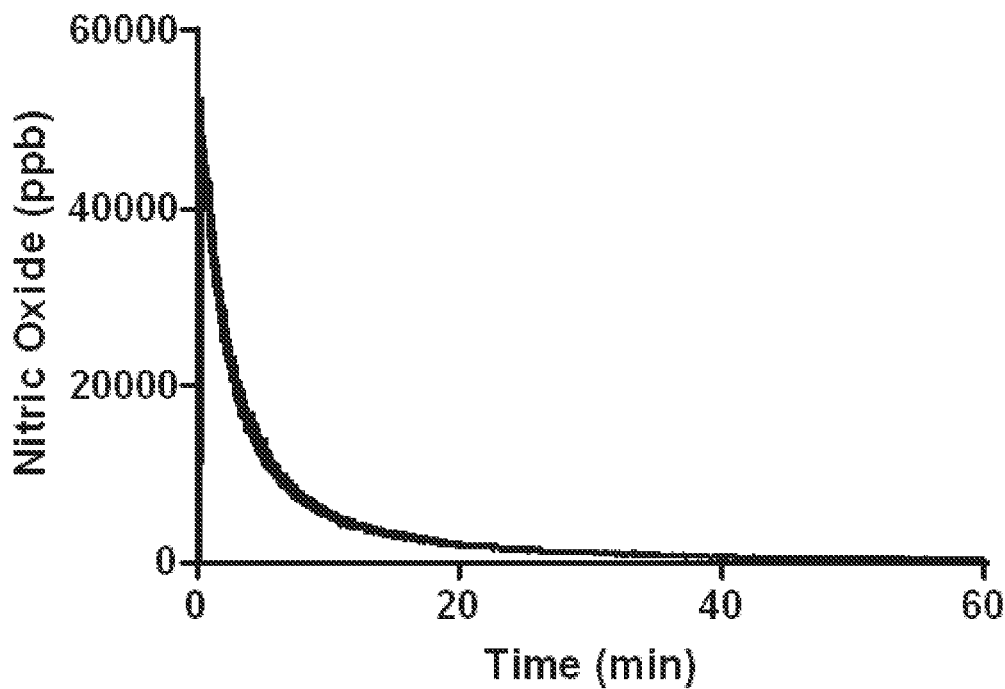
FIG. 7 is a graph of nitric oxide (ppb) measurement data obtained by introducing 5 mL of a nitric oxide releasing solution into a nitric oxide collection device as represented in FIG. 2.
Figure 8:
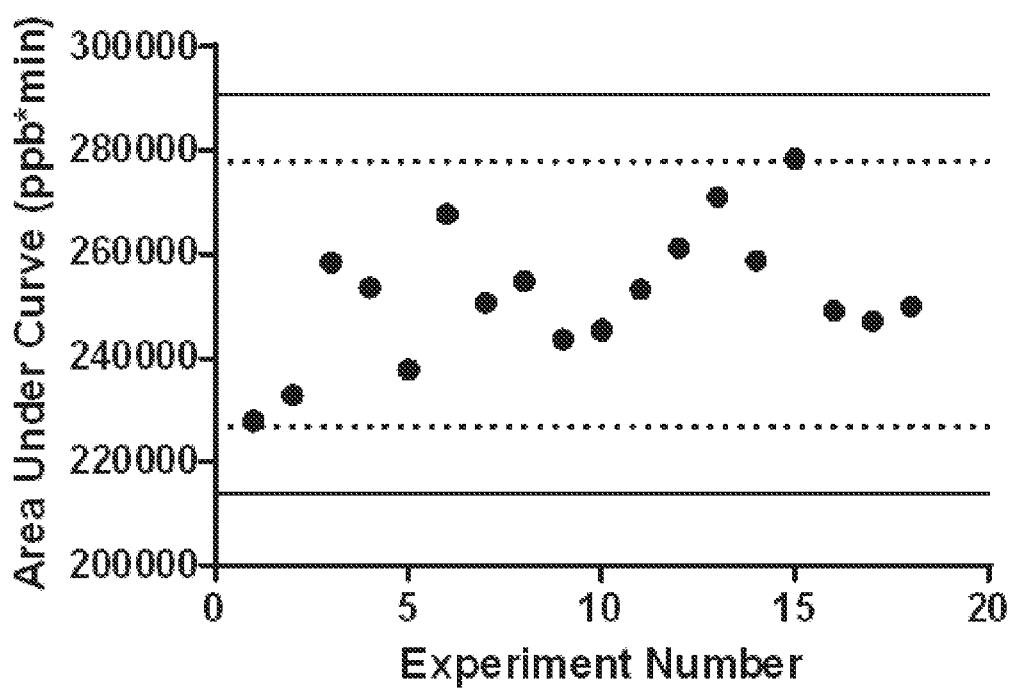
FIG. 8 represents the area under the curve (ppb*min) of NO calculated by introducing 5 mL of a nitric oxide releasing solution into a nitric oxide collection device as represented in FIG. 2; with each measurement lasting for 60 minutes and warning (dotted) and failure (solid) lines added signifying two and three standard deviations respectively.

FIG. 3 depicts the amount of NO (ppb) measured using the flow-over device. FIG. 4 depicts the maximum NO peak (ppb) obtained from injecting 5 mL of a nitric oxide releasing solution into the flow over device. FIG. 5 depicts the amount of NO production (ppb) after 30 minutes of measuring, obtained from injecting 5 mL of a nitric oxide releasing solution into the flow-over device. FIG. 6 depicts the slope (ppb/min) calculated from 1-30 minutes post injection, obtained from injecting 5 mL of a nitric oxide releasing solution into the flow-over device. FIG. 7 depicts the amount of NO (ppb) measured using the bubbler-type device obtained by injecting 5 mL of a nitric oxide releasing solution into the device. FIG. 8 depicts the area under the curve (ppb*min) calculated by injecting 5 mL of a nitric oxide releasing solution into the bubbler-type device. Each measurement was performed for 60 minutes. These results are summarized below in Table 1.

In further detail, the flow-over device was attached to a stand in a horizontal position. The inlet was connected to an inert gas (nitrogen) at a flow rate of 1 L/min. The exit was connected to a tube that was connected to a chemiluminescence NO analyzer. For the first method, NORS was prepared by mixing citric acid with a sodium nitrite solution. Five milliliters of the prepared NORS was injected into the flow-over device and the data was collected for 30 minutes. Data was analyzed using GraphPad Prism 6. Each time point was repeated three times. For the second method, 2.5 mL sodium nitrite was injected into the flow-over device. Afterwards 2.5 mL of citric acid was injected into the flow-over device. The combination of the two solutions prepared a NORS solution that was otherwise equivalent to the pre-prepared NORS. Data was collected for 30 minutes. Data was analyzed using GraphPad Prism 6. Each time point was repeated three times.

Figure 9:
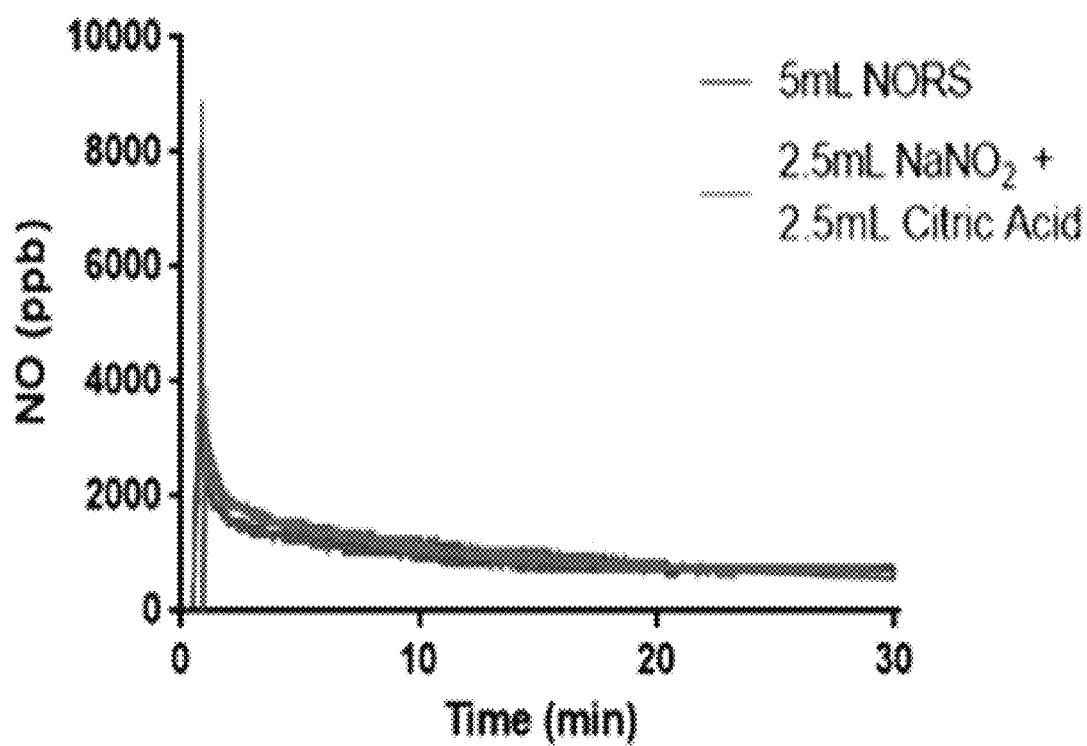
FIG. 9 is a graph of nitric oxide production data obtained by introducing 5 mL of a nitric oxide releasing solution into a nitric oxide collection device as represented in FIG. 1 and measured for 30 minutes including chemiluminescence in comparison to data obtained in an identical manner by introducing 2.5 mL of sodium nitrite followed by an injection of 2.5 mL of citric acid with each process repeated three times.

Data obtained from chemiluminescence detector is shown in FIG. 9. Specifically, NO production was measured using the flow-over device and chemiluminescence detection when either 5 mL of a nitric oxide releasing solution was injected and measured for 30 minutes or 2.5 mL of sodium nitrite was first injected then 2.5 mL of citric acid was injected and measured for 30 minutes. Each method was repeated three times.

Figure 10:
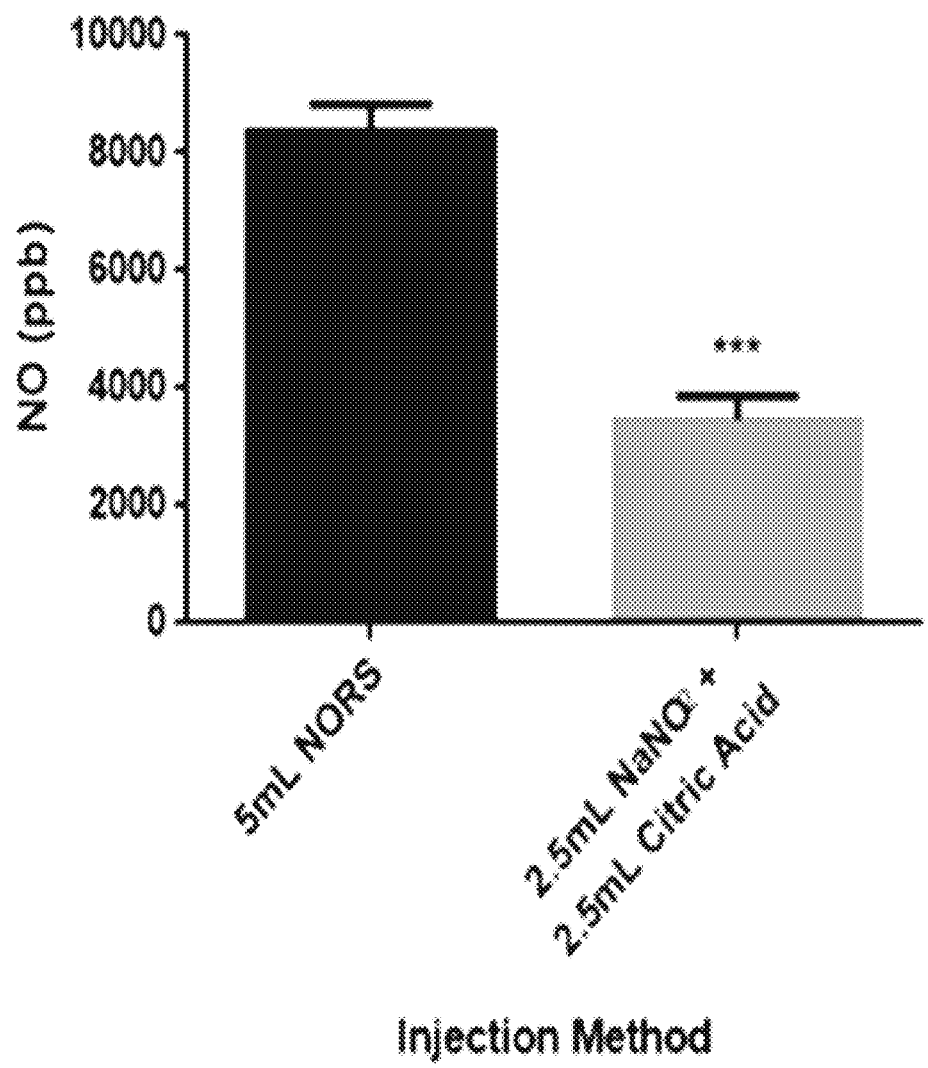
FIG. 10 is a bar graph comparing nitric oxide peaks data measured using a nitric oxide collection device as represented in FIG. 1 and chemiluminescence by introducing 5 mL of a nitric oxide releasing solution as compared to introducing 2.5 mL of sodium nitrite followed by 2.5 mL of citric acid and each method repeated three times quantified by a t-test for statistical analysis and significance marked with an asterisk (***=$p<0.001$)

As presented in FIG. 10, the second method (2.5 mL sodium nitrite+2.5 mL citric acid injections) had a significantly smaller peak relative to the first method of injection (5 mL NORS). A t-test was used for statistical analysis. Significance is marked with an asterisk (***=$p<0.001$).

Figure 11:
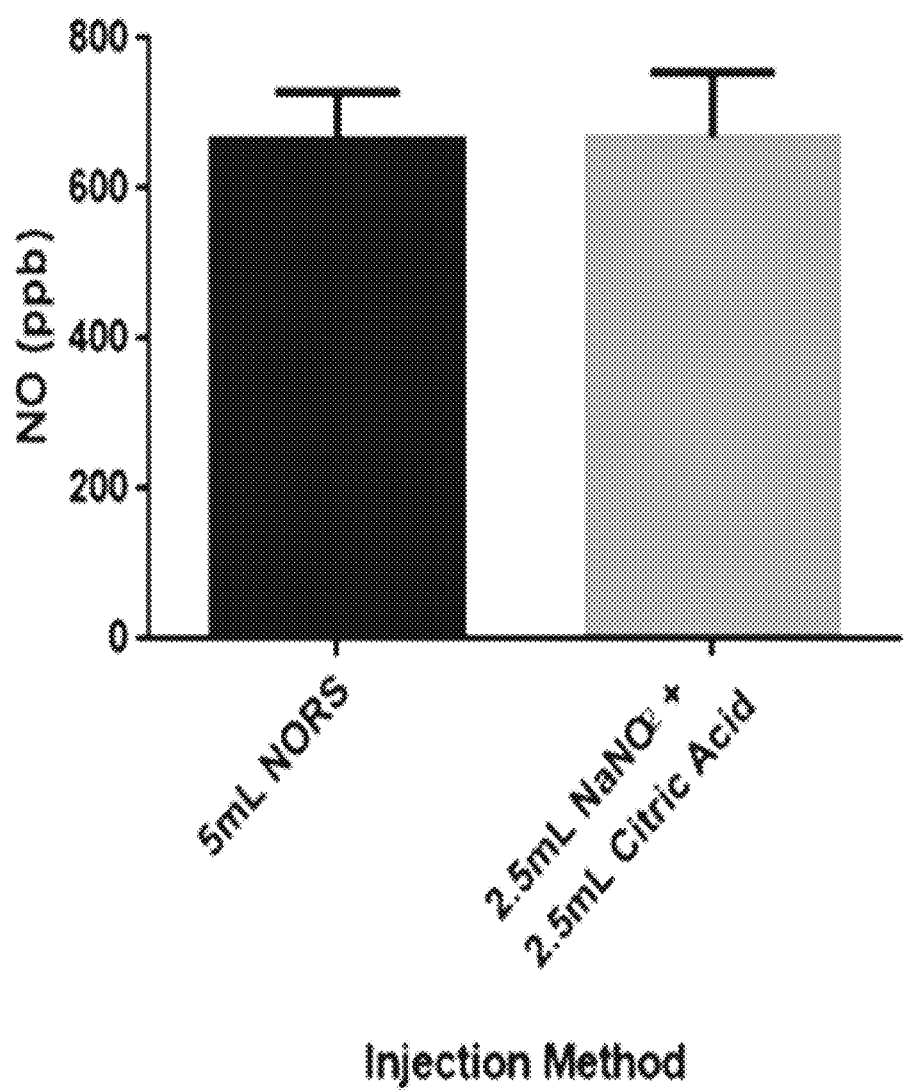
FIG. 11 is a bar graph comparing nitric oxide production 30 minutes after sample introduction of 5 mL of a nitric oxide releasing solution and measuring for 30 minutes using a nitric oxide collection device as represented in FIG. 1 and chemiluminescence, as compared to introduction of 2.5 mL of sodium nitrite followed by 2.5 mL of citric acid and measured for 30 minutes, with each method being repeated three times and a t-test used for statistical analysis.
Figure 12:
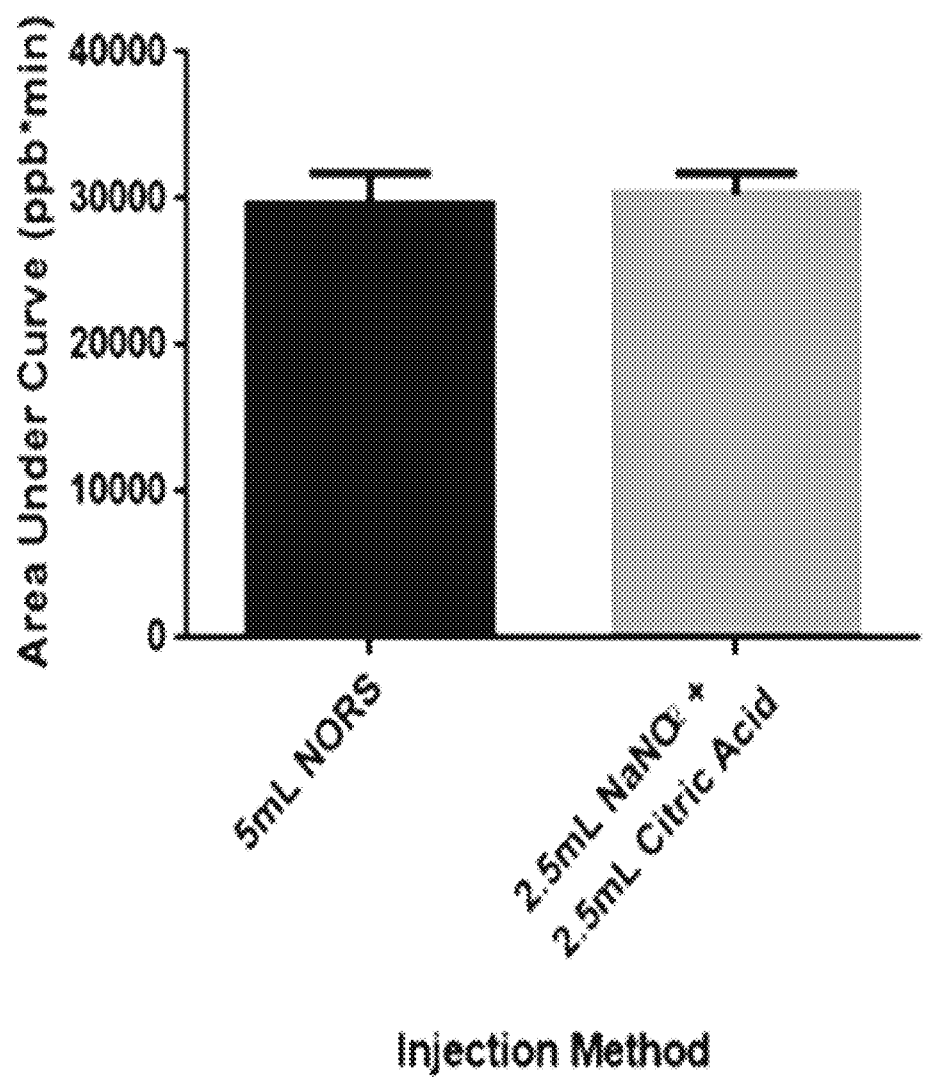
FIG. 12 is a bar graph comparing areas under the curve (AUC) after 30 minutes of measuring using a nitric oxide collection device as represented in FIG. 1 and chemiluminescence by introducing 5 mL of a nitric oxide releasing solution in comparison to introducing 2.5 mL sodium nitrite followed by 2.5 mL citric acid measured for 30 minutes, each repeated three times and quantified by a t-test for statistical analysis.

As presented in FIGS. 11 and 12, no significance was found after 30 minutes of NO production (FIG. 11) and the area under the curve after 30 minutes of measuring (FIG. 12). A t-test was used for statistical analysis to show that no significance (e.g. no significant difference) was found.

Thus, the only parameter with significant difference was the peak of NO release. The added energy from injecting NORS may cause more NO to be initially produced. However, these differences are short lived and the curve from both methods follow a similar pattern of release.

TABLE 1

Mean and ranges at ±2 σ (warning) and ±3 σ (failure) for each measurement. Data for max peak, 30 min measurement and slope (1-30 min) were obtained using the flow-over glass vessel and data for the area under the curve was obtained using the bubbler glass vessel.

|  | Device used | −3 σ | −2 σ | Mean | +2 σ | +3 σ |
|---|---|---|---|---|---|---|
| Max Peak | Flow Over | 1402 | 3708 | 8322 | 12936 | 15243 |
| Value at 30 min (ppb) | Flow Over | 341.8 | 413.3 | 556.4 | 699.4 | 770.9 |
| Slope (1-30 min) flow over device | Flow Over | −35.4 | −32.6 | −27.1 | −21.6 | −18.8 |
| AUC* | Bubbler | 213886 | 226688 | 252293 | 277897 | 290699 |

*Area Under Curve represent total NO released during the first 60 min, in PPM * min

Example 2—Quantifying Nitric Oxide Production from Different NORS Samples

In this example, two different injection methods for injecting a NORS into the flow-over device were explored. One method included injecting a pre-prepared NORS solution in the flow-over device. The other method included separately injecting a sodium nitrite solution and a citric acid solution into the flow-over device to produce a NORS solution within the sampling chamber. The peaks, NO production after 30 minutes, and area under the curve for both of the compositions was compared.

Example 3—Using Nitric Oxide Sampling Chambers to Characterize NORS Formulations The following method was developed in order to determine a consistent, repeatable link between NO production within NORS and the effective antimicrobial dose previously established with gas. This approach allowed indirect confirmation, in a reproducible way, of the amount of NO escaping from liquid phase into the headspace from any given NORS concentration. A constant flow of 3 liters per min (LPM) of nitrogen was chosen as the background carrier gas introduced into the sampling chamber. A sidestream (250 cc/min) chemiluminescent analyzer was used to sample the resulting distal gas concentration from the sampling chamber in ppm. Various nitrite strengths of 32 mL of NORS were tested to determine which would generate at least 160 ppm per 3 LPM. Once the appropriate nitrite concentration was identified then further in vitro dosing and toxicological studies were also performed to confirm equivalency with the effective antimicrobial dose previously established with gas (data not shown).

Figure 13:
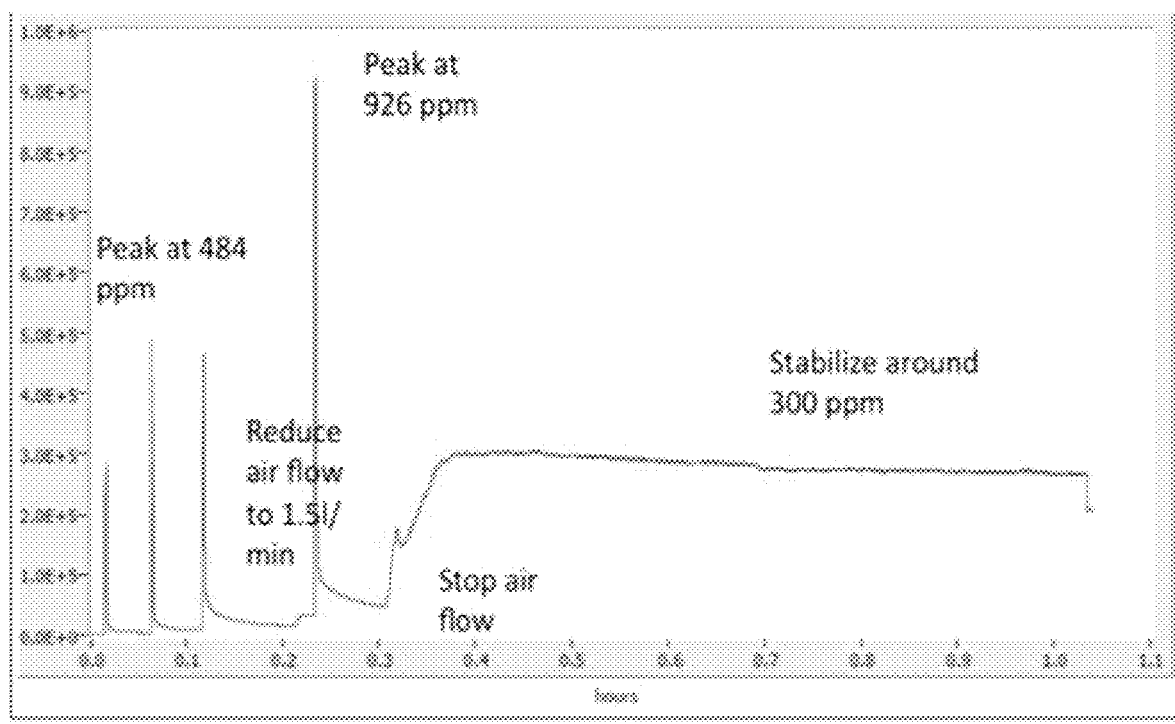
FIG. 13 is a representative graph of NO data measured by chemiluminescence after introducing 32 ml of a nitric oxide releasing solution into a sampling chamber.

In further detail, FIG. 13 is a representative graph of NO measurement by chemiluminescence after spraying 32 ml of NORS into the sampling chamber. Each spray into the sampling chamber resulted in a peak corresponding to NO gas. At 3 LPM, single sprays of NORS resulted in maximum peak of 926 ppm and each peak was reduced within 10 sec to the baseline. Successive sprays demonstrated an additive effect. After each spray baselines became a bit higher. However, when gas flow was stopped, the baseline of NO measured stabilized at 300 ppm for the time measured (an hour) with nominal drop of in NO production. This methodology, once validated in a cGMP environment, allows for various specifications of NORS ingredients to be validated, stability to be determined, and supply sources to be qualified.

EXAMPLE EMBODIMENTS

In one example there is provided a method of measuring nitric oxide release from a material, comprising: introducing a continuous flow of a carrier gas into a sample holding chamber via a carrier gas inlet at an effective flow rate; introducing an amount of a nitric oxide releasing material into the sample holding chamber via a sample inlet to contact the continuous flow of the carrier gas; directing the carrier gas and any released nitric oxide out of the sample holding chamber via an outlet to a nitric oxide detector; and quantifying an amount of released nitric oxide using the nitric oxide detector.

In one example of a method of measuring nitric oxide release from a material, the carrier gas is an inert carrier gas.

In one example of a method of measuring nitric oxide release from a material, the inert carrier gas is selected from nitrogen gas, a noble gas, helium gas, argon gas, neon gas, krypton gas, xenon gas, radon gas and combinations thereof.

In one example of a method of measuring nitric oxide release from a material, the effective flow rate is from about 0.025 liters per minute (L/min) to about 10 L/min.

In one example of a method of measuring nitric oxide release from a material, the method further comprises reducing oxygen content within the sample holding chamber to less than 5%.

In one example of a method of measuring nitric oxide release from a material, wherein reducing oxygen content comprises applying a vacuum to the sample holding chamber, flushing the sample holding chamber with an inert gas, or a combination thereof.

In one example of a method of measuring nitric oxide release from a material, reducing oxygen content comprises purging the sample holding chamber of oxygen.

In one example of a method of measuring nitric oxide release from a material, the carrier gas is introduced into the sample holding chamber through a single carrier gas inlet.

In one example of a method of measuring nitric oxide release from a material, the carrier gas is introduced into the sample holding chamber through a plurality of carrier gas inlets simultaneously.

In one example of a method of measuring nitric oxide release from a material, introducing the carrier gas is performed prior to introducing the nitric oxide releasing material.

In one example of a method of measuring nitric oxide release from a material, introducing the nitric oxide releasing material is performed prior to introducing the carrier gas.

In one example of a method of measuring nitric oxide release from a material, a first component of the nitric oxide releasing material is introduced prior to introducing the carrier gas and a second component of the nitric oxide releasing material is introduced after introducing the carrier gas.

In one example of a method of measuring nitric oxide release from a material, the carrier gas is directed to flow over the nitric oxide releasing material.

In one example of a method of measuring nitric oxide release from a material, the carrier gas is bubbled into the nitric oxide releasing material.

In one example of a method of measuring nitric oxide release from a material, the nitric oxide releasing material comprises a liquid, a semi-solid, a gel, or a cream.

In one example of a method of measuring nitric oxide release from a material, the nitric oxide releasing material is introduced in an amount of from about 1 microliter (µl) to about 1000 milliliters (ml).

In one example of a method of measuring nitric oxide release from a material, nitric oxide is directed toward the nitric oxide detector via a sidestream channel.

In one example of a method of measuring nitric oxide release from a material, nitric oxide is directed toward the nitric oxide detector via a mainstream channel.

In one example of a method of measuring nitric oxide release from a material, nitric oxide is sampled from the mainstream channel and transferred to the nitric oxide detector for analysis.

In one example of a method of measuring nitric oxide release from a material, nitric oxide is sampled directly from the sample holding chamber and transferred to the nitric oxide detector for analysis.

In one example of a method of measuring nitric oxide release from a material, an analysis time for each sample of nitric oxide releasing material is from about 1 minute to about 24 hours.

In one example of a method of measuring nitric oxide release from a material, the method further comprises regulating a temperature of the sample holding chamber to a temperature of from about 5° C. to about 40° C.

In one example of a method of measuring nitric oxide release from a material, the method further comprises agitating the sample holding chamber.

In one example of a method of measuring nitric oxide release from a material, the nitric oxide releasing material is prepared prior to introducing the nitric oxide releasing material into the sample holding chamber.

In one example of a method of measuring nitric oxide release from a material, the nitric oxide releasing material is activated within the sample holding chamber.

In one example of a method of measuring nitric oxide release from a material, nitric oxide is quantifiable at a level of 10 parts per billion or lower.

In one example there is provided a nitric oxide collection device, comprising: a sample holding chamber having an interior surface that is substantially inert to nitric oxide, said sample holding chamber being configured to receive a nitric oxide releasing material; a sample inlet configured to allow passage of a nitric oxide releasing material into the sample holding chamber; a carrier gas inlet in fluid communication with the sample holding chamber; and a nitric oxide outlet in fluid communication with the sample holding chamber.

In one example of a nitric oxide collection device, the interior surface comprises an inert liner positioned to line the interior surface of the holding chamber.

In one example of a nitric oxide collection device, the inert liner comprises an epoxy polymer, phenol epoxy, a vinyl polymer, a rubber, polyamide-imide (PAM), an acrylic polymer, polytetrafluoroethylene, or a combination thereof.

In one example of a nitric oxide collection device, the sample holding chamber is defined by a single unitary structure.

In one example of a nitric oxide collection device, the sample holding chamber is defined by plurality of structures coupled together.

In one example of a nitric oxide collection device, the plurality of structures comprises a nitric oxide receptacle and a lid.

In one example of a nitric oxide collection device, the sample inlet comprises a stopper, a septum, a filter, a syringe, a needle, or a combination thereof.

In one example of a nitric oxide collection device, the sample inlet comprises a separately-formed channel extending into the sample holding chamber.

In one example of a nitric oxide collection device, the sample inlet is contiguously formed with the sample holding chamber.

In one example of a nitric oxide collection device, the carrier gas inlet comprises a plurality of carrier gas inlets.

In one example of a nitric oxide collection device, the plurality of carrier gas inlets are positioned at angles relative to one another to promote homogenous mixing of the carrier gas within the sample holding chamber.

In one example of a nitric oxide collection device, the carrier gas inlet comprises a separately-formed fluid channel extending into the sample holding chamber and having a porous terminus positioned within the sample holding chamber.

In one example of a nitric oxide collection device, the carrier gas inlet is contiguously formed with the sample holding chamber.

In one example of a nitric oxide collection device, the device further comprises a mass flow meter positioned and configured to measure an inlet flow of a carrier gas flowing into the sample holding chamber.

In one example of a nitric oxide collection device, the device further comprises a diffuser positioned and configured to substantially homogenously disperse the carrier gas within the sample holding chamber.

In one example of a nitric oxide collection device, the nitric oxide outlet comprises a separately-formed fluid channel extending from within the sample holding chamber to an area external to the sample holding chamber.

In one example of a nitric oxide collection device, the nitric oxide outlet is contiguously formed with the sample holding chamber.

In one example of a nitric oxide collection device, a mass flow meter is positioned and configured to measure an outlet flow exiting the sample holding chamber.

In one example of a nitric oxide collection device, the device further comprises a temperature sensor configured to measure a temperature of or within the sample holding chamber.

In one example of a nitric oxide collection device, the device further comprises a temperature regulator configured to control a temperature within the sample holding chamber.

In one example of a nitric oxide collection device, the device further comprises an oxygen sensor configured to measure oxygen content within the sample holding chamber.

In one example of a nitric oxide collection device, the device further comprises an $NO_2$ sensor configured to measure $NO_2$ content within the sample holding chamber.

In one example of a nitric oxide collection device, the carrier gas inlet, the nitric oxide outlet, or both have an interior surface that is inert to NO.

In one example of a nitric oxide collection device, the interior surface of the carrier gas inlet, the nitric oxide outlet, or both are lined with an inert liner.

In one example of a nitric oxide collection device, the carrier gas inlet, the nitric oxide outlet, or both have an exterior surface that is inert to NO.

In one example of a nitric oxide collection device, the exterior surface of the carrier gas inlet, the nitric oxide outlet, or both are lined with an inert liner.

In one example there is provided a nitric oxide measurement system, comprising: a nitric oxide collection device according to any one of the above-recited examples and a nitric oxide detector fluidly coupled to the nitric oxide collection device.

In one example of a nitric oxide measurement system, the nitric oxide detector comprises a chemiluminescence detector, an electrochemical detector, a fluorescence detector, a mass spectrometer, or a combination thereof.

In one example of a nitric oxide measurement system, the system is configured to have a limit of quantitation for nitric oxide of 10 parts per billion or less.

In one example of a nitric oxide measurement system, the system is configured to quantify nitric oxide at levels of at least 1000 parts per million.

In one example of a nitric oxide measurement system, the nitric oxide detector is coupled to the nitric oxide collection device via a sidestream channel.

In one example of a nitric oxide measurement system, the nitric oxide detector is coupled to the nitric oxide collection device via a mainstream channel.

In one example of a nitric oxide measurement system, the system further comprises a carrier gas source fluidly coupled to the nitric oxide collection device.

In one example of a nitric oxide measurement system, the carrier gas source is an inert carrier gas source.

While the forgoing examples are illustrative of the specific embodiments in one or more particular applications, it will be apparent to those of ordinary skill in the art that numerous modifications in form, usage and details of implementation can be made without departing from the principles and concepts articulated herein. Accordingly, no limitation is intended except as by the claims set forth below.

What is claimed is:

1. A method of measuring nitric oxide release from a material, comprising:
    introducing a continuous flow of a carrier gas into a sample holding chamber via a carrier gas inlet at an effective flow rate;
    introducing an amount of a nitric oxide releasing material into the sample holding chamber via a sample inlet to contact the continuous flow of the carrier gas, wherein the sample holding chamber has a reduced oxygen content to less than 5%;
    directing the carrier gas and any released nitric oxide out of the sample holding chamber via an outlet to a nitric oxide detector; and
    quantifying an amount of released nitric oxide using the nitric oxide detector.

2. The method of claim 1, wherein the effective flow rate is from about 0.025 liters per minute (L/min) to about 10 L/min.

3. The method of claim 1, wherein reducing oxygen content comprises either applying a vacuum to the sample holding chamber, flushing the sample holding chamber with an inert gas, or a combination thereof, or purging the sample holding chamber of oxygen.

4. The method of claim 1, wherein the carrier gas is introduced into the sample holding chamber through a plurality of carrier gas inlets simultaneously.

5. The method of claim 1, wherein introducing the carrier gas is performed either prior to or after introducing the nitric oxide releasing material.

6. The method of claim 1, wherein a first component of the nitric oxide releasing material is introduced prior to introducing the carrier gas and a second component of the nitric oxide releasing material is introduced after introducing the carrier gas.

7. The method of claim 1, wherein the nitric oxide releasing material comprises a liquid, a semi-solid, a gel, or a cream.

8. The method of claim 1, wherein the nitric oxide releasing material is introduced in an amount of from about 1 microliter (µl) to about 1000 milliliters (ml).

9. The method of claim 1, wherein nitric oxide is either:
    directed toward the nitric oxide detector via either a sidestream channel or a mainstream channel;
    sampled from the mainstream channel and transferred to the nitric oxide detector for analysis; or
    sampled directly from the sample holding chamber and transferred to the nitric oxide detector for analysis.

10. The method of claim 1, wherein nitric oxide is quantifiable at a level of 10 parts per billion or lower.

\* \* \* \* \*